(12) United States Patent
Frayling et al.

(10) Patent No.: US 10,369,569 B2
(45) Date of Patent: Aug. 6, 2019

(54) METHOD OF IDENTIFYING DROPLETS IN A STACK AND AN ASSOCIATED SEQUENCER

(71) Applicant: BASE4 INNOVATION LTD, Cambridge, Cambridgeshire (GB)

(72) Inventors: Cameron Alexander Frayling, Cambridge (GB); Thomas Henry Isaac, Cambridge (GB)

(73) Assignee: BASE4 INNOVATION LTD, Cambridge, Cambridgeshire (GB)

( * ) Notice: Subject to any disclaimer, the term of this patent is extended or adjusted under 35 U.S.C. 154(b) by 76 days.

(21) Appl. No.: 15/574,005

(22) PCT Filed: Jul. 14, 2017

(86) PCT No.: PCT/EP2017/067851
§ 371 (c)(1),
(2) Date: Nov. 14, 2017

(87) PCT Pub. No.: WO2018/011398
PCT Pub. Date: Jan. 18, 2018

(65) Prior Publication Data
US 2018/0264475 A1    Sep. 20, 2018

(30) Foreign Application Priority Data
Jul. 14, 2016    (EP) .................... 16179518

(51) Int. Cl.
*B01L 3/00* (2006.01)
*G01N 21/64* (2006.01)
(Continued)

(52) U.S. Cl.
CPC ....... *B01L 3/502784* (2013.01); *B01L 3/0268* (2013.01); *C12Q 1/6869* (2013.01);
(Continued)

(58) Field of Classification Search
CPC ............ C12Q 1/6869; C12Q 2535/107; C12Q 2535/122; C12Q 2563/159;
(Continued)

(56) References Cited

U.S. PATENT DOCUMENTS

| 2002/0001546 A1 | 1/2002 | Hunter et al. |
| 2003/0087309 A1* | 5/2003 | Chen .................... B01J 19/0046 435/7.1 |

(Continued)

FOREIGN PATENT DOCUMENTS

WO    2014/151658    9/2014

OTHER PUBLICATIONS

Hindson et al., "High-Throughput Droplet Digital PCR System for Absolute Quantitation of DNA Copy Number", Analytical Chemistry, vol. 83, No. 22, 2011, pp. 8604-8610 (Year: 2011).*

(Continued)

*Primary Examiner* — Jennifer Wecker
(74) *Attorney, Agent, or Firm* — Wenderoth, Lind & Ponack, L.L.P.

(57) ABSTRACT

Disclosed is a method of identifying the contents of individual droplets in a droplet stream each droplet containing fluorophores in an initial non-fluorescing state characterized by the steps of introducing the droplets one-by-one into at least one open-ended tube to create a stack of droplets therein; activating the fluorophores within the droplets to cause them to fluoresce; releasing each droplet in the droplet stack in turn from the tube and detecting along the major axis of the tube fluorescence associated with each droplet as it emerges. Also disclosed is a method suitable for sequencing a biopolymer characterized by the steps of (1) progressively digesting the biopolymer into an ordered stream of its constituent monomers; (2) converting the stream of monomers into a corresponding stream of monomer-containing (Continued)

Figure 1:
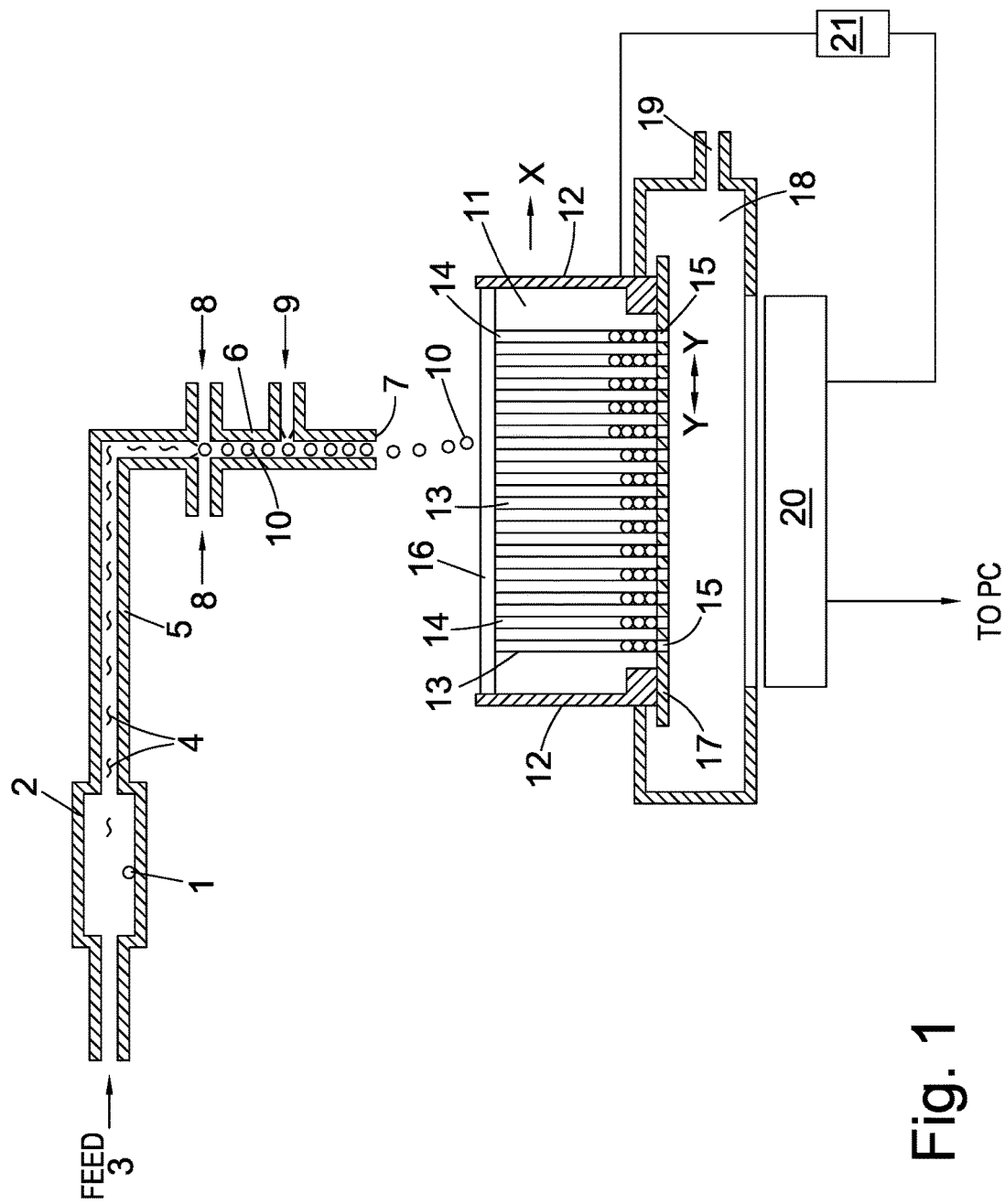

aqueous droplets each droplet additionally containing a probe capable of (a) capturing the monomer and (b) thereafter being digested to release an unqueched fluorophore characteristic of the captured monomer; (3) introducing the stream of droplets created in step (2) into an inlet end of at least one open-ended tube to create a stack of droplets therein and (4) releasing each droplet in turn from an outlet end of the tube(s) and detecting fluorophores in each droplet as each droplet emerges. The method may be used in a corresponding apparatus for sequencing a biopolymer such as a nucleic acid or protein.

29 Claims, 1 Drawing Sheet

(51) Int. Cl.
- *C12Q 1/6869* (2018.01)
- *B01L 3/02* (2006.01)
- *B01J 19/00* (2006.01)
- *C40B 60/12* (2006.01)

(52) U.S. Cl.
CPC ..... *G01N 21/6428* (2013.01); *G01N 21/6452* (2013.01); *B01J 2219/00367* (2013.01); *B01J 2219/00576* (2013.01); *B01J 2219/00702* (2013.01); *B01L 2200/0642* (2013.01); *B01L 2200/0673* (2013.01); *B01L 2300/0627* (2013.01); *B01L 2300/0867* (2013.01); *C40B 60/12* (2013.01); *G01N 2021/6439* (2013.01)

(58) Field of Classification Search
CPC ...... C12Q 2565/629; B01J 2219/00367; B01J 2219/00576; B01J 2219/00702; B01L 2200/0642; B01L 2200/0673; B01L 2300/0627; B01L 2300/0867; B01L 3/0268; B01L 3/502784; C40B 60/12; G01N 2021/6439; G01N 21/6428; G01N 21/6452

See application file for complete search history.

(56) References Cited

U.S. PATENT DOCUMENTS

| | | |
|---|---|---|
| 2011/0053798 A1 | 3/2011 | Hindson et al. |
| 2013/0225418 A1 | 8/2013 | Watson |
| 2014/0272996 A1 | 9/2014 | Bemis |

OTHER PUBLICATIONS

Written Opinion and International Search Report dated Aug. 25, 2017 in (PCT) Application No. PCT/EP2017/067851.

Hindson et al., "High-Throughput Droplet Digital PCR System for Absolute Quantitation of DNA Copy Number", Analytical Chemistry, vol. 83, No. 22, 2011, pp. 8604-8610.

Chang et al., "Self-alignment in the stacking of microchips with mist-induced water droplets" J. Micromech. Microeng., vol. 21, No. 1, 2011, pp. 1-11.

* cited by examiner

METHOD OF IDENTIFYING DROPLETS IN A STACK AND AN ASSOCIATED SEQUENCER

This invention relates to an improved method and device for identifying droplets in a droplet stack. It is useful inter alia for sequencing a biopolymer such as a nucleic acid by capturing its constituent monomer units in microdroplets before analysing them.

In our previously filed patent applications WO2014053854 and WO2014167323 we have disclosed a method for sequencing nucleic acids such as synthetic and naturally-occurring DNA and RNA by a method which involves first creating an ordered stream of single nucleotides from a corresponding precursor analyte; for example by progressive pyrophosphorolysis or exonucleolysis. Thereafter, the single nucleotides are captured in aqueous microdroplets where they are treated with a quenched, fluorophore-labelled oligonucleotide probe system which, after capture occurs, undergoes progressive exonucleolysis to liberate single nucleotides bearing unquenched fluorophores in a detectable state and whose characteristic fluorescence emissions enable the nucleotide originally captured to be reliably identified. Examples of probes and methods suitable for this purpose have been described in these and other patent applications including WO201405385 and WO2016012789.

Whilst the method described above can be carried out by creating and manipulating a stream of the droplets dispersed for example in an immiscible carrier medium such as silicone oil, we have recently found that the method can advantageously and more efficiently be performed by printing the droplets directly onto the surface of a planar substrate as they are formed. We have described variants of this droplet printing and storage method in US 2016122802 and European patent application EP15002007.1.

One potential drawback with this approach is that, because of the very large numbers of droplets involved when large nucleic acid fragments are being analysed, the substrate needs to be very large and in fact on occasion multiple substrates may be required. This is especially so when the original analyte comprises the many thousand or even millions of nucleotides characteristic of an organism's gene or chromosome. To overcome this drawback we have invented a method in which the printed droplets, rather than being stored on the surface of a substrate, are stacked in capillary tubes disposed within it until analysis is ready to take place. The droplets are then, at an appropriate time, caused to emerge from tubes at which point they may be analysed spectroscopically as we have taught previously. By this means we have been able to significantly reduce the size of an important part of a corresponding sequencer we are developing. Furthermore. we believe that the method has more general utility in the sorting of droplets in large droplet streams on the basis of their individual fluorescence characteristics.

Thus in a first aspect of the present invention there is provided a method of identifying the contents of individual droplets in a droplet stream each droplet containing fluorophores characterised by the steps of introducing the droplets one-by-one into an at least one open-ended tube to create a stack of droplets therein; releasing each droplet in the droplet stack in turn from the tube and detecting along the major axis of the tube fluorescence associated with each droplet as it emerges.

In one embodiment the method includes the additional step of characterising or sorting the droplets on the basis of the fluorescence detected including for example using one or more sorting gates, e.g. electro-mechanical gates, synchronised with the detection of a fluorescence signal. In another embodiment the droplets are introduced into an inlet end of the tube and removed from a corresponding outlet end. In another embodiment the tube is vertically aligned and the droplets are introduced into an inlet at the top and removed from the droplet stack an outlet end at the bottom.

In one preferred embodiment, the fluorophore-containing droplets are introduced into the tube in an initial quenched (non-fluorescing) state and the method includes the additional step of activating the fluorophores whilst the droplets are located within the droplet stack. In another embodiment, the fluorophores are associated with a probe molecule, for example an oligonucleotide probe, which is selective for and characteristic of an analyte molecule which the user wishes to identify indirectly. Further details concerning the nature of the tube(s), how they may be disposed (for example in a solid substrate), and the nature and contents of the droplets are explained in more detail below with specific reference to one suitable application of the method; the sequencing of biopolymers by characterising their constituent monomer units.

Thus in a second aspect of the invention there is provided a method suitable for characterising a biopolymer characterised by the steps of (1) progressively digesting the biopolymer into an ordered stream of its constituent monomers; (2) converting the stream of monomers into a corresponding stream of monomer-containing aqueous droplets each droplet additionally containing a probe capable of (a) capturing the monomer and (b) thereafter being digested to release an unquenched fluorophore characteristic of the captured monomer; (3) introducing the stream of droplets created in step (2) into an inlet end of at least one open-ended tube to create a stack of droplets therein and (4) releasing each droplet in turn from an outlet end of the tube(s) and detecting fluorophores in each droplet as each droplet emerges.

It will also be appreciated that this particular method may form the working basis of a corresponding sequencer suitable for sequencing a biopolymer such as a nucleic acid or a protein. Thus according to a third aspect of the invention there is provided an apparatus for sequencing a biopolymer characterised by comprising:

a digestion unit including an analyte-receiving location where the biopolymer is progressively digested into a corresponding stream of its constituent monomers;

a dispensing unit including at least one droplet-dispensing nozzle for dispensing the stream of monomers as a corresponding stream of droplets;

a substrate through which is provided an array of open-ended tubes each having an inlet and an outlet on opposing faces and whose major axes are disposed parallel to the direction in which the droplets are to be dispensed;

a means for stepping the droplet-dispensing nozzle(s) across the inlet face of the substrate in at least one direction perpendicular to the major axes of the tubes thereby allowing the droplets to be dispensed into the tubes;

a controller for creating a droplet stack in the tubes and for releasing droplets from the stack through the outlets as required;

at least one source of electromagnetic radiation adapted to illuminate the outlets in the outlet face of the substrate;

a means for synchronising the illumination of the outlets with the emergence of the droplets therefrom and at least one photodetector adapted to detect synchronised fluorescence radiation signals arising from the outlets.

In one embodiment the biopolymer is a nucleic acid and the monomer units are nucleotides; for example nucleoside triphosphates, nucleoside diphosphates or nucleoside monophosphates. In another embodiment the biopolymer is a protein and the monomers are amino acid molecules.

Considering step (1) of the method of the second aspect of the invention, which is carried out in the digestion unit of the corresponding sequencer, in one embodiment, where the biopolymer is a nucleic acid, it is effected by progressive pyrophosphorolysis or exonucleolysis of a precursor nucleic acid analyte. In the corresponding sequencer this will occur at an analyte-receiving location in the digestion unit where for example the analyte is attached to the wall of a chamber or microfluidic channel either directly or via an intermediate element such as a functionalised bead adapted to be held at the location by for example suction or magnetic attraction.

The nucleic acid analyte can in principle be any nucleic acid of natural or synthetic origin including fragments of DNA or RNA of any nucleotide chain length up to that found in a gene or chromosome. In one embodiment, where the DNA or RNA is of natural origin, the nucleic acid is comprised of nucleotides bearing one of the characteristic nucleobases thymine (T), adenine (A), cytosine (C), guanine (G) and uracil (U). For further information on the range and scope of other nucleic acids, nucleotides and nucleobases which can be analysed by the method and apparatus of the present invention the reader is directed to those of our patent applications referred to above.

In one embodiment, the nucleic acid analyte is digested by progressive pyrophosphorolysis or progressive exonucleolysis in an aqueous medium into a corresponding ordered stream of either single nucleoside triphosphates or single nucleoside monophosphates where the ordering corresponds to the nucleotide sequence of the analyte. This digestion is suitably effected in a flowing medium containing the necessary reagents and enzymes disclosed in those of our patent applications referred to above. Preferably the nucleotides are nucleoside triphosphates produced by progressive pyrophosphorolysis of the analyte in the presence of pyrophosphate and a polymerase exhibiting the relevant pyrophosphorolytic behaviour. In one embodiment, downstream of the digestion unit there is provided a zone comprising a chamber or a fluidic junction whereby by an inorganic pyrophosphatase may be introduced to hydrolyse any residual pyrophosphate ion.

In step (2) of the method, which is designed to be carried out in the dispensing unit of the sequencer, the stream of nucleotides is converted into a corresponding ordered stream of nucleotide-containing aqueous droplets. In theory, each droplet in the stream may contain a nucleotide derived from the nucleotide-containing stream. However to ensure that each filled droplet contains one and only one nucleotide it is generally preferred to adjust the rate of droplet generation relative to the flow rate of the nucleotide-containing stream so that each filled droplet in the droplet stream is separated by a number of empty ones. In one embodiment each filled droplet in the stream is separated by from 1 to 20 preferably 2 to 10 empty ones.

In addition to the nucleotide, each droplet in the droplet stream suitably contains a probe capable of capturing the nucleotide introduced thereinto. In practice, for DNA and RNA this means that the droplet will contain 1, 2, 3 or 4 different probe types each selective for a different characteristic nucleobase and bearing a correspondingly different fluorophore type. Examples of preferred probe types include those described in our applications WO2014053853, WO2014053854, WO2014167323, and WO2016012789 to which the reader is directed for further information as to their nature and synthesis. Common characteristics of all these probe types are that (1) they are adapted to selectively capture single nucleotides in the presence of enzymes such as ligase and polymerase; (2) in their unused state they are resistant to exonucleolysis but can be readily exonucleolytically digested after their corresponding single nucleotide has been captured and (3) that they are comprised of characteristic fluorophores which remain quenched until the used probe or a component therefore is digested. Thus, if in addition to the probes and the nucleotide, each droplet further contains enzymes capable of exhibiting ligase, polymerase and exonuclease behaviour the observer will see a growth in a fluorescence signal characteristic of the particular nucleotide captured in each droplet after a period of incubation. Especially preferred are multi-component oligonucleotide probes comprising (a) a first single-stranded oligonucleotide labelled with characteristic fluorophores in a quenched state and (b) second and third single-stranded oligonucleotides capable of hybridising to complementary regions on the first oligonucleotide in the presence of a target single nucleoside triphosphate, a ligase and a polymerase to thereby create an essentially double-stranded used probe. Thereafter, the first-single stranded component of the used probe can be exonucleolytically digested to release the fluorophores in an unquenched and therefore detectable state. In one preferred embodiment, the second and third single-stranded oligonucleotides are oligonucleotide regions connected together by a linker region which itself may be comprised of nucleotides. In this embodiment, capture of the target nucleotide by the probe creates a closed-circle single-stranded oligonucleotide component including the second and third regions which is itself highly resistant to exonucleolysis. Thereafter, in both cases and once the first oligonucleotide component has been digested to release its fluorophores, the other oligonucleotide strand can then hybridise to and create further used probes in a cyclic process which ensure a rapid growth in the fluorescence signal. Further information concerning these probes, suitable fluorophores and quenchers and the capture methodology can be found in WO2016012789.

Suitably the droplets created in step (2) of the process and in the dispensing unit of the sequencer are microdroplets having a finite diameter of less than 100 microns, preferably less than 50 microns, more preferably less than 20 microns and even more preferably less than 15 microns. Most preferably of all their diameters are in the range 2 to 20 microns. In one embodiment, the microdroplet generation rate employed in step (2) of the method and the dispensing unit is in the range 50 to 3000 microdroplets per second preferably 100 to 2000.

Any suitable method can be used to create the droplet stream from the nucleotide-containing stream which will be reflected in the design of the dispensing unit. In one embodiment the dispensing unit consists of a chamber attached to one or more droplet-dispensing nozzle(s) for dispensing the droplets into the inlet of the tube(s) in step (3). In one embodiment of this design, multiple feed-lines may be attached adjacent or directly to the nozzle(s); one of which comprises the aqueous nucleotide-containing stream from step (a) with others being for the probe and the various enzymes and other chemical reagents required.

Mixing in or near the nozzle head then ensures that each droplet dispensed contains a nucleotide and all the components needed for the probe to function. In another embodiment, the nozzle(s) may be used to create a droplet stream from the nucleotide-containing stream and the other components added thereafter; for example by microinjection, picoinjection or by coalescing each droplet with similar secondary droplets containing the other components subsequently printed on top of them on the surface of the substrate before they are introduced into the open tubes by action of the controller.

In step (3) of the method, the stream of droplets containing the nucleotide and the various probe components are introduced into at least one tube to create a stack of droplets one on top of another. To ensure the ordering of the droplets is preserved in the stack the internal diameter of the tube(s) should be less than twice the diameter of the droplets. In one embodiment and in order to preserve the integrity of the droplets the tube(s) are prefilled with a water-immiscible solvent such as silicone oil. In another embodiment, to facilitate movement of the droplets through the tube as stacking occurs the internal surface(s) of the tube(s) are provided with a hydrophobic coating or preferably one comprised of hydrophobic and hydrophilic regions. To facilitate reliable detection of the fluorescence in the droplet in step (4) below, it is preferred that the refractive indices of the aqueous medium comprising the droplets and the solvent are in the range 1.3 to 1.4 and 1.3 to 1.7 respectively. Typically the choice of refractive index for the solvent will be determined by that of the aqueous medium which in turn will be dependent on the exact concentration of the probe and other reagents contained in the droplet(s). In one embodiment the tube(s) may comprise one or a bundle of hollow-core optical fibres.

Suitably the droplets are caused to be drawn into the tube(s) by application of a negative pressure to the outlet. This can most conveniently be achieved by applying suction to a region or chamber connected to the outlet region of the tube(s). In one embodiment, once a given tube's droplet stack has been created, the negative pressure can removed until such time as step (4) takes place. This enables the droplets to undergo a period of incubation in the stack between steps (3) and (4) during which a fluorescence capability is allowed to develop through action of the various enzymatic processes associated with application of the probe.

In one preferred embodiment of step (3) which is utilised in the sequencer defined above an array of open-ended tubes disposed in a substrate is employed. The inlets and outlets of these tubes are then disposed on opposed inlet and outlet faces of the substrate with the inlet face being disposed immediately beneath the droplet-dispensing nozzles. The major axes of the tubes then extend in a direction parallel to the direction of droplet dispensing. In one embodiment the alignment is in a vertical plane allowing the tubes to be filled by action of gravity and/or suction. In one embodiment the substrate is a sheet or block of material such as metal, semiconductor, plastic or glass with a regular array of capillary tubes disposed therein. In one preferred embodiment the substrate itself is a silicon, glass or plastic block into which the capillaries have been fabricated and in another the internal surfaces of these capillaries are coated as explained above. Suitably the glass or plastic substrate is treated so that it has a degree of light absorbance. In one preferred embodiment the glass substrate has a refractive index in the range 1.4 to 1.7 preferably 1.45 to 1.65.

To enable the tubes to be filled by the droplet-dispensing nozzle(s) the sequencer includes a means for stepping the droplet-dispensing nozzle relative to the inlet face of the substrate in at least one direction perpendicular to the major axes of the tubes; suitably along both of the axes perpendicular thereto. Methods of doing this will be readily apparent from a consideration of conventional printer technology. In one embodiment the nozzles may be mounted on an assembly moveable in two dimensions relative to a fixed substrate by computer-controlled electric motors; in an alternative embodiment the substrate is mounted on such an assembly and the location of the printer nozzle(s) are fixed. In yet another embodiment both nozzles and substrate are mounted on separate moveable assemblies.

Associated with the substrate is a controller for creating a droplet stack in each tube and releasing the droplets from each tube as required. As explained above such a controller, which is suitably computer-controlled, may include a suction device for creating the negative pressure and a means for switching the negative pressure on and off as required. It will also preferably include a series of micro-electro-mechanical gates associated with each tube outlet which can be opened and closed to control release of each droplet from the stack through the outlet. In one embodiment these gates comprise micro-electro-mechanical valves or a perforated plate moveable across the outlet face.

In one embodiment there may be associated with the outlet face metal particles or a layer of metal capable of undergoing plasmonic resonance under the influence of incident electromagnetic radiation. By this means the fluorescence signal from the fluorophores in each droplet can be enhanced further with a consequential improvement on the accuracy of the apparatus as well as reducing the droplet cross-talk mentioned below.

In step (4) of the method the droplets are released in turn from the stack at an outlet end of the tube(s) to enable the fluorophores contained therein to be detected as emergence occurs. Where the tube(s) are vertically aligned the outlet will be at the bottom of the stack. Detection of these fluorophores is suitably carried out by conventional means; i.e. illuminating each droplet with electromagnetic radiation of a wavelength capable of causing the fluorophores to fluoresce (e.g. visible or ultra-violet light). Thereafter a photodetector or like device is used to detect any fluorescence generated.

Illumination of the droplet is suitably carried out in a substantially direction parallel to the major axes of the tubes in which case there is a risk in certain circumstances of the fluorescence signal detected being complicated by secondary fluorescence signals emitted by droplets in the rest of the stack behind the droplet being investigated. The fluorescence signal 'cross-talk' this phenomenon creates can be substantially managed, reduced or even eliminated by careful choice of the relative refractive indices of the droplet, solvent and glass substrate from within the ranges quoted above; the nature of the particular fluorophores used and to a certain extent the texture, polarisation and geometry of the substrate. In one embodiment a substrate made of darkened glass or of glass whose periphery has been black-coated is employed. In another, the substrate geometry is chosen so that it does not support long-range waveguide modes in the tubes; in other words any modes which are established are short-range and decay away over rapidly over a maximum of five adjacent droplets in the stack. Wave-guides may be employed to assist in achieving this. In one embodiment it is preferred that these parameters are optimised so that less than 10% preferably less than 5% signal cross-talk is observed. In another, the scattering of electromagnetic radiation from the droplet being detected inhibits the pick-up of electromagnetic radiation by the droplet(s) behind it in the stack for example by tuning the wave-guided modes in the tube(s).

In the sequencer defined above, the source of incident electromagnetic radiation is typically an LED, a laser or other high-intensity light source which can be focused on the areas containing the outlets by means of ancillary optics (lenses, mirrors etc.). Suitably the source is connected to a means for synchronising the illumination of the outlets with the emergence of the droplets from the outlet. In one embodiment this consists of a microprocessor for synchronising the source with the opening and closing of the micro-electro-mechanical gates.

Finally, the sequencer comprises at least one photodetector or the like to detect the synchronised fluorescence signal. Typically this component consists of an array of photodetectors designed to make synchronised measurements at all the outlets simultaneously. The signals produced by the photodetector(s) can then be assembled into a data stream which is transferred to a microprocessor or stand-alone PC for further analysis.

The method and a sequencer according to the invention are now illustrated with reference to the attached FIGURE which shows a sectional schematic diagram of a nucleic acid sequencer using the method of the present invention.

A sample of DNA attached to a bead 1 is subject to progressive pyrophosphorolysis by a polymerase in digestion chamber 2 through which an aqueous medium stream 3 containing pyrophosphate and the other reagents required to effect the digestion have been added. Downstream of 2, 3, now containing an ordered stream of single nucleotide triphosphates 4, passes via microfluidic tubing 5 to droplet dispensing unit 6 which includes a droplet-dispensing nozzle 7. Injector lines 8 feed silicone oil to the top of 6 where droplets 10 comprised of 3 are created and caused to flow past injector line 9 where a probe according to our patent application WO2016012789, inorganic pyrophosphatase and an exonuclease are introduced by picoinjection. Aqueous droplets 10 now having a refractive index of 1.3, at least some of which contain 4, are then caused to issue forth from 7 where they are dispensed in turn onto a block or sheet of substrate 11. 11 is made of light-absorbing dark glass having a refractive index of 1.5 and is mounted on assembly 12 which is moveable in at least the direction X indicated by the arrow. 11 is further provided with a rectangular array of open-ended capillary tubes 13 each of which is provided with inlet and outlet orifices 14 and 15. In its unused state, the inlet face of 11 and tube 13 are respectively coated and filled with silicone oil 16 of refractive index 1.5. The diameters of 13 are 1.75 times the diameter of the droplets 10.

Immediately below the outlet face of 11 is a perforated plate 17 which is moveable back and forth along the axis Y-Y' using an electric motor (not shown) to partially open and close the outlet orifices 15. The outlet face of 11 is enclosed within chamber 18 to which a suction can be remotely applied via tube 19 and a computer-controlled pump (not shown) to establish a negative pressure between each 14 and 15. By this means, and with each 15 partially closed by 17, each droplet 10 is dispensed into each inlet orifice 14 through 16, where it is drawn into its tube 13 and stacked until each tube is full. Thereafter 11 is returned to its starting position and the contents of 10 left to incubate for a period of time.

When the contents of droplets 10 are ready to be analysed, 17 is actuated (by sideways motion relative to 11) to open and close each 15 thereby allowing each 10 in the stack to be drawn out of 13 in turn and onto the surface of 11 immediately beneath 17. Synchronous with the opening and closing of 17 the released droplets are illuminated with a source of high intensity coherent light such as a laser (not shown) slightly off-axis from that of the tubes which causes the active fluorophores in each released 10 to fluoresce. Also synchronous with this any fluorescence back-scattered in a direction parallel to 15 detected by an array of photodetectors 20 associated with each 15 so that a multiplicity of nucleotide-characteristic signals are generated which may be assembled into a data stream for analysis by a microprocessor (not shown) in order to reconstruct the sequence of 1. Synchronisation is achieved by means of microprocessor 21.

The invention claimed is:

1. A method of identifying the contents of individual droplets in a droplet stream wherein each droplet contains fluorophores, the method comprising the steps of: (a) introducing the droplets one-by-one into at least one open-ended tube to create a stack of droplets therein; (b) releasing each droplet in the droplet stack in turn from the tube; and (c) detecting along a major axis of the tube fluorescence associated with each droplet as each droplet emerges.

2. The method of claim 1, wherein the droplets are introduced into an inlet end of the tube and released from an outlet end.

3. The method of claim 1, wherein the tube is vertically aligned and each droplet is released from the bottom of the droplet stack via the outlet end.

4. The method of claim 1, wherein the fluorophores in the droplets are in an initial non-fluorescing state, and wherein the method further comprises a step of activating the fluorophores whilst the droplets are located within the droplet stack.

5. The method of claim 1, wherein the fluorophores are associated with a probe molecule which is selective for and characteristic of an analyte molecule which is to be identified.

6. The method of claim 1, further comprising an additional step of sorting or characterising the droplets by the fluorescence signal detected.

7. The method of claim 1, wherein a negative pressure is applied across the tube whilst the tube is being filled with droplets from the inlet end.

8. The method of claim 1, wherein the tube has an internal diameter that is less than twice the diameter of the droplets.

9. The method of claim 1, wherein the droplets in the droplet stack are suspended in an immiscible solvent.

10. The method of claim 1, wherein the tube has an internal surface, and wherein the internal surface of the tube is provided with hydrophobic and hydrophilic coating regions.

11. The method of claim 9, wherein each droplet has a refractive index in the range 1.3 to 1.4 and the solvent has a refractive index in the range 1.3 to 1.7.

12. The method of claim 1, wherein an array of tubes disposed in parallel in a substrate is employed and a stack of droplets is created in each tube.

13. The method of claim 12, wherein the substrate is made of glass having a refractive index in the range 1.4 to 1.7 which is optionally light-absorbing.

14. The method of claim 1, further comprising a step of irradiating the tubes with electromagnetic radiation and detecting the fluorescence radiation signal arising therefrom as each droplet emerges.

15. The method of claim 13, wherein the refractive indices of the aqueous droplet, the solvent and glass are chosen so that guided modes are established which give rise to less than 10% cross-talk between the fluorescence signal generated by the emerging droplet and other droplets behind it in the stack.

16. The method of claim 14, wherein scattering of electromagnetic radiation from one droplet being detected inhibits pick-up of electromagnetic radiation by the other droplets behind the one droplet in the stack by tuning wave-guided modes in the tube.

17. A method as claimed in claim 1 suitable for characterising a biopolymer comprising the steps of (1) progressively digesting the biopolymer into an ordered stream of constituent monomers; (2) converting the stream of monomers into a corresponding stream of monomer-containing aqueous droplets, wherein each droplet additionally contains a probe capable of (a) capturing the monomer and (b) thereafter being digested to release an unquenched fluorophore characteristic of the captured monomer; (3) introducing the stream of droplets created in step (2) into an inlet end of at least one open-ended tube to create a stack of droplets therein; (4) releasing each droplet in turn from an outlet end of the tube(s); and (5) detecting fluorophores in each droplet as each droplet emerges.

18. The method as claimed in claim 17, further comprising a step of (6) removing the droplet from the outlet prior to repeating steps (4) and (5) on the next emerging droplet.

19. The method of claim 17, wherein the biopolymer is a nucleic acid and the monomers are nucleotides.

20. The method of claim 19, wherein the nucleic acid is DNA or RNA of natural or synthetic origin.

21. The method of claim 17, further comprising a period of incubation between steps (3) and (4).

22. An apparatus for sequencing a biopolymer comprising:
a digestion unit including an analyte-receiving location where the biopolymer is progressively digested into a corresponding stream of constituent monomers;
a dispensing unit including at least one droplet-dispensing nozzle configured for dispensing the stream of monomers as a corresponding stream of droplets;
a substrate through which is provided an array of open-ended tubes each having an inlet and an outlet on opposing faces and whose major axes are disposed parallel to the direction in which the droplets are to be dispensed;
a means for stepping the droplet-dispensing nozzle(s) relative to the inlet face of the substrate in at least one direction perpendicular to the major axes of the tubes thereby allowing the droplets to be dispensed into the tubes;
a controller programmed to create a droplet stack in the tubes for releasing the droplets from the stack through the outlets as required;
at least one source of electromagnetic radiation configured to illuminate the outlets in the outlet face of the substrate;
a means for synchronising the illumination of the outlets as the droplets emerge therefrom, and
at least one photodetector configured to detect synchronised fluorescence radiation signals arising from the outlets.

23. The apparatus of claim 22, further comprising a wave-guide associated with each tube for reducing or eliminating cross-talk fluorescence signals from secondary droplets in the droplet stack.

24. The apparatus of claim 22 further comprising a chamber or fluidic junction located between the digestion unit and the dispensing unit for introducing a pyrophosphatase.

25. The apparatus of claim 22, wherein the substrate is made of light absorbing glass having a refractive index in the range 1.45 to 1.65.

26. The apparatus of claim 22, wherein the tubes are capillaries comprising walls with hydrophobic and hydrophilic coating regions.

27. The apparatus of claim 22, wherein the controller includes a means for providing a negative pressure between the inlet and the outlet, and a micro-electro-mechanical gate which can be opened and closed to control release of each droplet from the droplet stack through the outlet.

28. The apparatus of claim 22, wherein the tubes are vertically aligned and the controller releases each droplet from the bottom of the droplet stack.

29. The method of claim 13, wherein the refractive index of the glass is chosen so that guided modes are established which give rise to less than 10% cross-talk between the fluorescence signal generated by the emerging droplet, and other droplets behind it in the stack.

* * * * *